Oct. 29, 1957 J. D. FLANDERS Re. 24,385

DISPOSABLE NAPKIN

Original Filed Dec. 14, 1953

INVENTOR.
Jay D. Flanders.
BY
Harold J. L. Vescovite
Atty.

United States Patent Office

Re. 24,385
Reissued Oct. 29, 1957

24,385

DISPOSABLE NAPKIN

Jay D. Flanders, Glendale, Calif.

Original No. 2,742,042, dated April 17, 1956, Serial No. 398,146, December 14, 1953. Application for reissue May 13, 1957, Serial No. 658,908

6 Claims. (Cl. 128—290)

Matter enclosed in heavy brackets [ ] appears in the original patent but forms no part of this reissue specification; matter printed in italics indicates the additions made by reissue.

This invention relates to articles for personal cleanliness and particularly to [an anal] *a disposable* napkin. *The napkin may, for example, be designed* for use by persons who by reasons of post-operative or other infirmity are afflicted with minor uncontrollable anal discharges which otherwise would soil clothing or be otherwise both costly and embarrassing.

The principal object of the invention is to provide an absorbent [anal] napkin which may be worn by the user without discomfort and without additional supporting means, which is inexpensive and disposable and which is effective for its intended use.

Figure 2:
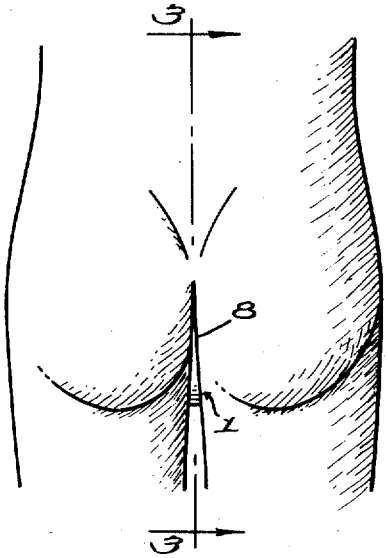
Figure 3:
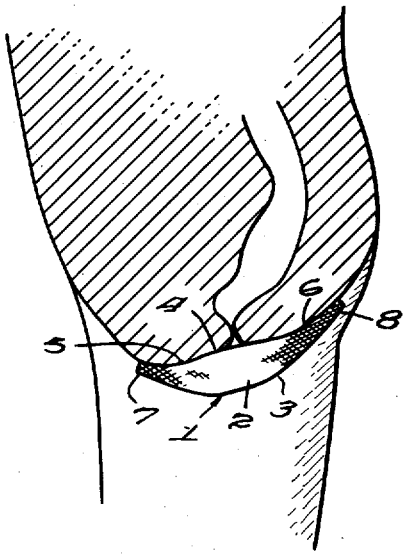
Figure 1:
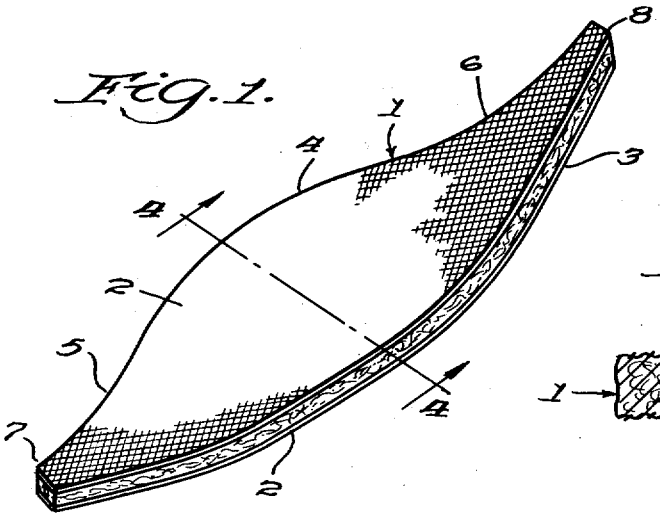
Figure 4:
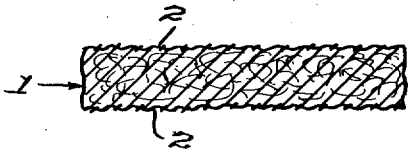

With the foregoing object in view, together with such additional objects and advantages as may subsequently appear, the invention resides in the provision of [an anal] *a disposable, absorbent* napkin in which the foregoing object is realized in practice; a satisfactory mode of execution of the invention being described in the following specification by way of example; reference being had to the accompanying drawings which form a part of said specification and in which drawings:

Fig. 1 is a perspective view of an anal napkin [embodying] *illustrating one embodiment of* the present invention, Figs. 2 and 3 are, respectively, rear and side elevations showing the napkin in position of use; Fig. 3 being shown as a section taken on the line 3—3 of Fig. 2, and Fig. 4 is a sectional view taken on the line 4—4 of Fig. 1.

Referring to the drawings, the invention comprises a flat pad 1 of irregular shape formed of absorbent material such as cellulose fiber material or of absorbent cotton, the latter preferably having light weight cloth facing members 2, 2 of the same shape in plan outline applied to the opposite faces thereof. If desired, the pad may be impregnated with a suitable deodorant in dry form.

The pad as viewed in plan is of greater length than width and comprises a convexly curved outer or rear edge 3, an opposed more sharply convexly curved inner edge portion 4 of lesser length than the outer edge 3 and centrally disposed with respect to the length of the pad; the said inner edge portion 4 at each end thereof being concavely curved as at 5 and 6 and continuing from said concavely curved portions to form tapered end portions 7 and 8. The shape of the pad as above described is such as to be substantially the same in shape and area as those portions of the [body] *crotch* of the user which continually contact each other at the sides of the anal declivity and which comprise the skin covering the maximi glutei.

In use, the *illustrated* napkin is applied while the person is in a sitting position and is positioned with the highest portion of the curved edge 4 directly opposing the anus. On standing erect, the pad will be gripped by the opposite sides of the anal declivity and securely held in position by such gripping action (see Fig. 2). Referring to Fig. 3, it will be noted that the inner edge portions 4, 5 and 6 closely follows the curvature of the innermost portion of the anal declivity while the outer edge 3 generally follows the curved line representing the outermost points of contact of the skin forming the anal declivity. Thus, the maximum [available] extent of body surface available is utilized to serve to hold the napkin in place *within the crotch* and experiment has demonstrated that once thus positioned, it will remain in place until it is intentionally removed. Further, it is to be noted that the maximum area of the pad is positioned to be adjacent to the point of anal discharges to be absorbed thereby.

While absorbent cotton and the like may be used for the pad material, the less costly cellulose fiber materials which are more readily disintegrated by water are to be preferred. The pads are inexpensive to manufacture and are therefore capable of being offered at prices which make the use thereof by persons requiring the protection afforded by the use of the pads, a practical possibility.

*Various features of the present invention are obviously applicable to various other types of disposable napkins.*

I claim:

1. As an article of manufacture, an anal napkin comprising an absorbent pad of substantially uniform thickness adapted for insertion edgewise into the human anal declivity; said pad having a side surface contour substantially approximating in size and shape the area of contact of the opposed skin surfaces forming the human anal declivity.

2. As an article of manufacture, a disposable anal napkin comprising a pad of uniform thickness adapted to be inserted edgewise into the human anal declivity; said pad being formed of an absorbent material which is subject to disintegration in water; said pad having a side surface contour substantially approximating in size and shape the area of contact of the opposed and normally contacting body surfaces forming the human anal declivity.

3. As an article of manufacture, a self supporting and disposable anal napkin comprising a pad of uniform thickness adapted to be inserted edgewise into the human anal declivity; said pad being formed of an absorbent material which is subject to disintegration in water; said pad having a side surface contour which substantially approximates the area of contact of the opposed and normally contacting body surfaces which form the anal declivity of a human being; said pad being adapted to be held in the said declivity by being gripped by the said opposed body surfaces.

*4. As an article of manufacture, a disposable absorbent napkin comprising a pad of substantially uniform thickness adapted to be inserted edgewise into the human crotch, said pad having a side surface contour substantially approximating in size and shape the area of contact of the opposed and normally contacting body surfaces forming the human crotch.*

*5. As an article of manufacture, a self supporting and disposable napkin comprising a pad of substantially uniform thickness adapted to be inserted edgewise into the human crotch, said pad being formed of an absorbent material which is subject to disintegration in water, said pad having a side surface contour substantially approximating the area of contact of the opposed and normally contacting body surfaces which form the crotch of a human being, said pad being adapted to be held in said crotch by being gripped by said opposing body surfaces.*

*6. As an article of manufacture, a disposable absorbent napkin comprising a pad of substantially uniform thickness adapted to be inserted edgewise into the human crotch, said pad having a side surface contour of such size and shape as to be capable of being held in the crotch*

*by gripping action of opposed body surfaces forming the crotch.*

References Cited in the file of this patent or the original patent

UNITED STATES PATENTS 2,064,431 Jorgenson ---------- Dec. 15, 1936

2,629,381 Brown ---------- Feb. 24, 1953
2,682,875 Brown ---------- July 6, 1954

FOREIGN PATENTS 595,971 France ---------- July 31, 1925